United States Patent [19]

Errico et al.

[11] Patent Number: 5,575,792
[45] Date of Patent: Nov. 19, 1996

[54] EXTENDING HOOK AND POLYAXIAL COUPLING ELEMENT DEVICE FOR USE WITH TOP LOADING ROD FIXATION DEVICES

[75] Inventors: Joseph P. Errico, Far Hills; Thomas J. Errico, Summit; James D. Ralph, Oakland, all of N.J.

[73] Assignee: Fastenetix, L.L.C., Summit, N.J.

[21] Appl. No.: 542,529

[22] Filed: Oct. 13, 1995

Related U.S. Application Data

[63] Continuation-in-part of Ser. No. 502,803, Jul. 14, 1995.
[51] Int. Cl.$^6$ .................................................. A61B 17/70
[52] U.S. Cl. .............................................. 606/61; 606/72
[58] Field of Search ............................... 606/61, 69, 70, 606/71, 72, 73, 66, 65, 60, 59, 54, 104

[56] References Cited

U.S. PATENT DOCUMENTS

| | | | |
|---|---|---|---|
| 4,805,602 | 2/1989 | Puno et al. | |
| 4,946,458 | 8/1990 | Harms et al. | 606/61 |
| 4,987,892 | 1/1991 | Krag et al. | 606/61 |
| 5,005,562 | 4/1991 | Cotrel | 606/61 X |
| 5,067,955 | 11/1991 | Cotrel | 606/61 |
| 5,122,131 | 6/1992 | Tsou | 606/61 |
| 5,176,680 | 1/1993 | Vignaud et al. | 606/61 |
| 5,190,543 | 3/1993 | Schläpfer | 606/61 |
| 5,207,678 | 5/1993 | Harms et al. | 606/61 |
| 5,217,497 | 6/1993 | Mehdian | 623/17 |
| 5,261,909 | 11/1993 | Sutterlin et al. | 606/61 |
| 5,261,912 | 11/1993 | Frigg | 606/61 |
| 5,306,275 | 4/1994 | Bryan | 606/61 |
| 5,360,431 | 11/1994 | Puno et al. | 606/72 |
| 5,437,671 | 8/1995 | Lozier et al. | 606/61 |
| 5,443,467 | 8/1995 | Biedermann et al. | 606/65 |

*Primary Examiner*—Guy V. Tucker
*Attorney, Agent, or Firm*—Joseph P. Errico

[57] ABSTRACT

A lamina hook device which has a rod receiving body portion of variable length. Selected embodiments include a polyaxial coupling element so that the rod receiving channel thereof may be angulated. In each embodiment, the blade portion has a cylindrical recess and the body includes a shaft portion which is slideably mounted therein. The top of the cylindrical recess is slotted, threaded, and tapered to receive a tightening nut. The tightening crush locks the shaft in the recess. In a first embodiment, the upper portion of the body includes a channel in which a rod is a disposed. The rod is locked within the channel by means of a top locking nut or an optional rod securing sleeve. In a second embodiment, the shaft has a semi-spherical head on which a separate coupling element, having a lower and an upper portion, is mounted. The lower portion has a slotted exterior taper and a semi-spherical interior chamber in which the head is initially polyaxially disposed. The upper portion has a channel therein for receiving the rod and a threading for receiving a top locking nut. A locking ring is disposed about the coupling element, at the top thereof, being initially positioned above the bottom of the channel such that the rod seats against the top of the locking ring. As in the first embodiment, a locking nut is provided, along with an optional rod securing sleeve to lock the rod in the recess; the process of doing which causes the locking ring to descend, crush locking the head in the interior chamber.

20 Claims, 7 Drawing Sheets

EXTENDING HOOK AND POLYAXIAL COUPLING ELEMENT DEVICE FOR USE WITH TOP LOADING ROD FIXATION DEVICES

CROSS-REFERENCE TO PRIOR APPLICATION

This invention is a continuation-in-part of application, U.S. Ser. No. 08/502,803, filed Jul. 14, 1995, still pending, entitled "A Polyaxial Locking Screw And Coupling Element Assembly For Use With Rod Fixation Apparatus".

BACKGROUND OF THE INVENTION

1. Field of the Invention

This invention relates generally to a spinal fixation device comprising a hook and coupling element assembly for attaching to the posterior lamina portion of the spine and for receiving and holding securely a rod of an implantation apparatus using same. More specifically, this invention relates to a hook and coupling element assembly having a variable height body portion.

2. Discussion of the Prior Art

The bones and connective tissue of an adult human spinal column consist of an upper portion having more than 20 discrete bones, and a lower portion which consists of the sacral bone and the coccygeal bodies. The bones of the upper portion are generally similar in shape, as will be more fully described hereinbelow with respect to FIGS. 1 and 2. Despite their similar shape, however, they do vary substantially in size in accordance with their individual position along the column and are, therefore, anatomically categorized as being members of one of three classifications: cervical, thoracic, or lumbar. The cervical portion, which comprises the top of the spine, up to the base of the skull, includes the first 7 vertebrae. The intermediate 12 bones are the thoracic vertebrae, and connect to the 5 lumbar vertebrae.

These bones of the upper portion vary in size, but are each similarly coupled to the next by a tri-joint complex. The tri-joint complex consists of an anterior disc and the two posterior facet joints, the anterior discs of adjacent bones being cushioned by cartilage spacers referred to as intervertebral discs. Referring now to FIGS. 1 and 2, top and side views of a typical vertebral body of the upper portion of the spinal column is shown. The spinal cord is housed in the central canal 10, protected from the posterior side by a shell of bone called the lamina 12. The lamina 12 has three large protrusions, two of these extend laterally from the side ends thereof and are referred to as the transverse process 14. The third extends back and down from the center of the lamina and is called the spinous process 16.

The anterior portion of the spine comprises a set of generally cylindrically shaped bones which are stacked one on top of the other. These portions of the vertebrae are referred to as the vertebral bodies 20, and are each separated from the other by the intervertebral discs 22. Pedicles 24 are bone bridges which couple the anterior vertebral body 20 to the corresponding lamina 12 and posterior elements 14,16.

The lower portion of the spinal column, which extends into the hip region is primarily comprised of the sacral bone. This bone is unlike the other bones of the spinal column, in both shape and size. In fact, at birth humans have five distinct sacral bones which begin to fuse together during childhood, and by adulthood have fully combined. For the purpose of describing this invention, however, the sacral bone shall be referred to as distinct from the spinal column; the spinal column, therefore, comprising for the purposes of this description, only the cervical, thoracic, and lumbar vertebrae.

In its entirety, the spinal column is highly complex in that it houses and protects critical elements of the nervous system which have innumerable peripheral nerves and arterial and veinous bodies in close proximity. In spite of these complexities, the spine is a highly flexible structure, capable of a high degree of curvature and twist through a wide range of motion. Genetic or developmental irregularities, trauma, chronic stress, tumors, and disease, however, can result in spinal pathologies which either limit this range of motion, or which threaten the critical elements of the nervous system housed within the spinal column.

A variety of systems have been disclosed in the art which achieve this immobilization by implanting artificial assemblies in or on the spinal column. These assemblies may be classified as anterior, posterior, or lateral implants. As the classification suggests, lateral and anterior assemblies are coupled to the anterior portion of the spine, which is the sequence of vertebral bodies. Posterior implants are attached to the back of the spinal column, generally by coupling to the pedicles via screws, or by means of hooks which attach under the lamina and entering into the central canal. In either case, the implants generally comprise elongate support rod elements which are coupled to the screws or hooks to immobilize several sequential vertebrae, for example to hold them stable so that the adjacent bones may be fused with bone graft. The prior co-pending application, U.S. Ser. No. 08/502,803, of which this application is a continuation-in-part, discloses novel devices which provide significantly superior performance for such implants which comprise screws for coupling to the pedicles. The present invention relates to corresponding implant apparatus which utilize hooks.

Such hook and rod assemblies generally comprise a plurality of hooks having rounded blade portions, flat extending members of which are inserted posteriorly under the lamina between the transverse process and the spinous process. The hooks further include upper body portions to which the support rod may be coupled. The rod extends along the axis of the spine, coupling to each of a plurality of hooks via receiving portions of their bodies. The aligning influence of the rod forces the spine to which it is affixed, to conform to a more proper shape.

It has been identified, however, that a considerable difficulty may be associated with inserting hooks under sequential lamina along a misaligned curvature and simultaneously exactly positioning their rod receiving portions such that they are aligned so that the rod can be passed therethrough without distorting, tilting, rotating, or exerting undesired translational forces on the hooks. Correction of this difficulty requires the time consuming and difficult tasks of reshaping the rods or repositioning the hooks, each of which is understood to require considerably longer operating time, which is known to increase the incidence of complications associated with surgery.

It is often the case that the failure of the hook is related to the height of the body portion. More specifically, it is desirable to have hooks which have rod receiving means which are variable in height. It is, further, desirable to provide hooks which comprise variable angle, or polyaxial, coupling elements, such that the rod receiving means may be angulated or rotated to align with the rod.

It is, therefore, the principal object of the present invention to provide a lamina hook having a rod coupling body which provides for elongation of the body portion thereof, so that the rod receiving portion of the body may be moved relative to the hook.

It is further a principal object of the present invention to provide a lamina hook having a body portion having polyaxial freedom of implantation angulation with respect to rod reception.

In addition, it is an object of the present invention to provide such an assembly which comprises a reduced number of elements, and which correspondingly provides for expeditious implantation.

Accordingly it is also an object of the present invention to provide an assembly which is reliable, durable, and provides long term fixation support.

Other objects of the present invention not explicitly stated will be set forth and will be more clearly understood in conjunction with the descriptions of the preferred embodiments disclosed hereafter.

SUMMARY OF THE INVENTION

The preceding objects of the invention are achieved by the present invention which is a lamina hook having a variable height extending body portion and a blade portion to which the variable height body portion may be coupled. More particularly, the hook comprises a curvate flat hook shaped blade portion having a flat extending member at one end thereof for slipping under the lamina, and a second body coupling end having a cylindrically shaped recess in the top thereof. The cylindrical recess is oriented to be generally perpendicular to the axis of the spine. The top of the cylindrically shaped recess comprises a slotted opening so as to be selectively contractable by an inwardly directed radial force. The external surface of the body coupling end, which includes the slots also includes a taper, for example a narrower top. This tapered portion further comprises an external threading so that a nut may be introduced onto the threading; the tightening of which causes the selective contraction of the top of the cylindrical recess.

In a first embodiment, the body of the device comprises a top loading coupling element which includes an elongate lower shaft portion. The shaft portion is designed to be slidably and rotationally mounted within the cylindrical recess so that prior to being locked into place by tightening the top of the recess to the shaft, the coupling element may be rotationally varied relative to the blade portion, and raised or lowered within the cylindrical recess and relative to the blade. In a preferred variation of this embodiment, the shaft portion is restrained against full removal from the recess in the blade portion by means of a mutual track, guide rails, or equivalent feature.

The rod receiving upper portion of the coupling element has a channel formed in the top thereof, which, in conjunction with a top locking nut, secure the support rod to the coupling element. More specifically, with respect to the rod receiving portion of this first embodiment, the cylindrical body of the coupling element comprises a pair of upwardly extending members formed of the cylindrical body which define therebetween a vertically oriented channel, wherein the rod is retained.

The uppermost portion of the upwardly extending members have an external surface threading on which a top locking nut may be introduced. The bottom surface of the nut is designed to seat against the top surface of the rod securing sleeve. Engagement of the nut with the upper portion of the coupling element, and driving of the nut downward onto the upper portion of the coupling element causes the rod to be driven downward, locking it to the bottom curved surface of the channel so as to be secured against all rotational or translational motion relative to the channel.

An optional rod securing sleeve having a curved bottom may be disposed between the top locking nut and the rod to enhance rod gripping strength. The external rod securing sleeve is generally cylindrical in shape, having a hollow center for sliding over the top of the coupling element. The bottom of the sleeve includes two opposing downwardly extending members; forming therebetween a second channel. The sleeve, therefore, has a conformation which resembles an upside down U-shape and cups the rod from above. Subsequent to the placement of the rod in the channel, the rod securing sleeve is deposited on the coupling element such that the rod is positioned within the vertically aligned slots therein. The top locking nut therefore seats against a top surface of the rod securing sleeve and forces it downward onto the rod so as to again lock the rod in the channel.

In a preferred variation, the top of the rod receiving coupling element portion has a small threaded recess therein for receiving a threaded post for alignment and positioning prior to being locked into place.

The implantation of this first embodiment may begin with the positioning of the blade portion relative to the lamina, and more specifically by the placement of the flat extending member under the appropriate lamina and into the spinal canal. As stated above, in this proper position, the body mating end of the blade portion, and the cylindrical recess therein, are disposed above the lamina, oriented such that the recess is directed substantially posteriorly relative to the patient's spine, and generally transverse to the support rod to be coupled to the body portion.

Once in position, the surgeon may either insert the shaft of the coupling element into the recess to the appropriate depth, therein providing for the necessary length body, or, if the coupling element is pre-loaded in the recess and restrained from full withdrawl therefrom, simply raise the body out of the recess to the necessary extent. In either case, rotational adjustment of the shaft about the axis of insertion is also possible at this time. A tightening nut is then introduced onto the threading at the slotted and tapered top of the recess, and is tightened by rotation thereof until the slots in the tapered portion narrow, thereby rigidly locking the shaft within the recess. The direction and disposition of the tightening nut prior to the locking step varies with the specific embodiment, however, for the purposes of this description, the tightening nut is introduced from above. (In an alternative variation, the tightening nut could be pre-mounted to the exterior surface of the body receiving recess, and engage the threading from below. In such an embodiment, the taper of the upper portion of the body receiving portion would widen toward the top so that engagement of the tightening nut could selectively contract the opening by rotationally translating upwards on the threading.)

Once the shaft has been positioned and locked in place, the support rod may be inserted into the top channel of the rod coupling portion of the body, and the top locking nut engaged on the surface threading of the upwardly extending members. The final downward translation of the locking nut securely locks the rod within the recess via a crush-locking of the rod in the curved bottom of the channel.

In the variation of this embodiment in which a rod securing sleeve is used, the sleeve is introduced about the body and over the rod prior to the engagement of the top locking nut. The downward translation of the nut provides the locking force of the sleeve against the rod so that the rod is locked between the sleeve and the bottom of the channel.

In a second embodiment, the hook assembly comprises a similar blade portion, tightening nut, and shaft portion of the body, however, the top of the shaft comprises a semi-spherical ball on which an independent rod coupling element is polyaxially mounted as set forth more fully hereinbelow.

More specifically, the assembly may be divided into a blade portion, and shaft portion, and a rod coupling element portion. The rod coupling element may be further conceptually divided into a lower socket portion and and upper rod and nut receiving portion. The lower socket portion is designed with an interior chamber having an opening at the bottom of the coupling element. The interior chamber is provided for receiving therein the semi-spherical head of the shaft portion such that it and the coupling element are held together, but prior to the securing of the rod thereto, the coupling element remains free to swing and rotate freely with respect to the shaft and blade portions. The external surface of the socket portion includes at least one vertical slot which is provided so that the semi-spherical head, which has a major diameter which is larger than the opening in the bottom of the element may be received within the open volume therein. The at least one slot resiliently expands to receive the head and contracts into position once the head is fully inserted, therein inhibiting the head from being retracted.

The exterior of the lower portion of the coupling element, into which the head of the shaft is inserted, tapers outward slightly toward the bottom of the element, therein having a slightly wider bottom diameter than at the top of the lower portion. A locking ring, having a diameter equal to or greater than the top of the lower portion, but less than the diameter of the bottom of the lower portion, is disposed initially about the top of the lower portion.

Subsequent to proper positioning of the blade portion of the hook under the corresponding lamina, the shaft is locked to the blade portion as set forth with respect to the first embodiment. The coupling element is then angulated into the ideal position for receiving the support rod, and the locking ring may be forced by a sufficient application of pressure downward along the exterior of the lower portion of the coupling element. The locking ring therein applies an inward force against the walls of the interior chamber, and the corresponding narrowing of the vertical slots thereof. Once fully driven downward the locking ring causes the coupling element to be securely locked relative to the shaft portion, and in turn to the blade portion as well.

The upper portion of this polyaxial coupling element are similar to the rod receiving and coupling portions of the first embodiment, but for the channel in the top of this embodiment extending more deeply along the axial extent of the coupling element so that the rod initially seats against the top annular surface of the locking ring. The locking ring on the lower portion is initially positioned so that the upper annular surface thereof extends vertically above the bottom of the channel so that in its initial disposition in the channel, the rod seats on the locking ring. As the top locking nut descends along the threading on the upwardly extending members of the coupling element and onto the rod, the rod is driven downward, causing the locking ring to descend along the exterior of the lower section, crush locking the semi-spherical head of the shaft to the interior chamber of the coupling element. Ultimately the inward radial force applied to the lower portion of the coupling element by the locking ring causes the at least one slot therein to close and for the head of the shaft to be locked therewith. The rod, too, is then securely locked between the top of the locking ring and the bottom surface of the top locking nut, and is thereby prevented from axial or rotational movement.

As with the first embodiment, this embodiment may optionally include a rod securing sleeve which is introduced between the rod and the top locking nut to enhance the holding strength with respect to the rod. The sleeve element is substantially identical to the sleeve described above with respect to the first embodiment.

The implantation of this embodiment begins as the first embodiment did, with the positioning of the blade portion relative to the lamina wherein the flat extending member thereof is placed under the lamina. The shaft portion, which comprises a semi-spherical head, is locked within the cylindrical recess by the application of the tightening nut.

The coupling element is then angulated as is required for the ideal capturing and securing of the rod in the top channel thereof. Once the rod has been inserted in the channel, and is disposed on the top annular surface of the locking ring, the top locking nut is rotationally lowered along the threading of the upwardly extending members and seats against the top surface of the rod, causing the rod and the locking ring to be forced downward. The downward translation of the locking ring causes the lower portion to lock to the semi-spherical head of the shaft. In contrast to the first embodiment, in which the rod is locked in place between the bottom surface of the top locking nut (or rod securing sleeve) and the bottom of the channel, the top locking nut (or optional rod securing sleeve) and the locking ring secure the support rod therebetween, preventing rotational and translational motion thereof after locking.

It shall be understood that the coupling element may comprise an axial passageway, extending from the bottom of the channel to the interior chamber, such that a threaded post may be utilized to engage a threaded recess in the semi-spherical head of the shaft portion, such that the shaft portion and the coupling element may be provided to the surgeon as intially polyaxially coupled parts. The axial passageway and the recess in the semi-spherical head may be aligned so that the surgeon can raise and lower the shaft portion relative to the blade portion without disassembling the coupling element from the shaft.

Other aspects and features of the embodiments of this invention are provided hereinbelow in detail, with reference to the identified Figures.

DETAILED DESCRIPTION OF THE PREFERRED EMBODIMENT

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope.

Figure 3:
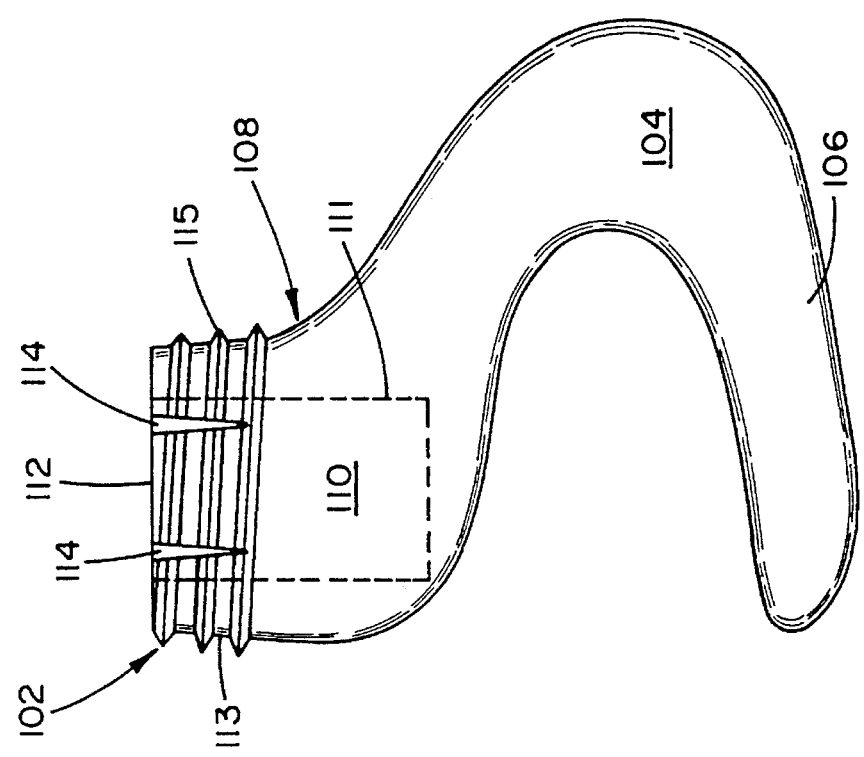
FIG. 3 is a side cross-sectional view of a blade portion of the hook of the present invention, said blade portion having a cylindrical recess in the top thereof.

Referring now to FIG. 3, the blade portion 100 of the present invention is shown wherein it comprises a body receiving portion 102 and a C-shaped portion 104. The lower extending branch 106 of the C-shaped portion 104 comprises a flat extending member which is understood to be the portion which is inserted under the lamina of the patient's spine. The body receiving portion 102 is positioned at the upper extending branch of the C-shaped portion 104 at the end 108 thereof.

The body receiving portion 102 comprises a cylindrically shaped recess 110 being defined by an inner tubular surface 111. The axis of the cylindrical recess 110 is oriented to be generally perpendicular to the axis of the spine, and transverse to the axis of the support rod of the implant apparatus. The top of the cylindrically shaped recess 110 comprises an opening 112 defined by the upper annular portion of the inner surface 111 and an outer annular surface 113. The opening further includes slots 114 so that the opening may be selectively narrowed by an inwardly directed radial force. The outer surface 113 of this opening 112 is tapered such that it widens as a function of distance from the opening. This tapered outer surface 113 further comprises an external threading 115 so that a nut may be introduced thereonto; the downward translation of which provides an inward radial force to contract the opening 112 of the cylindrical recess 110.

Figure 2:
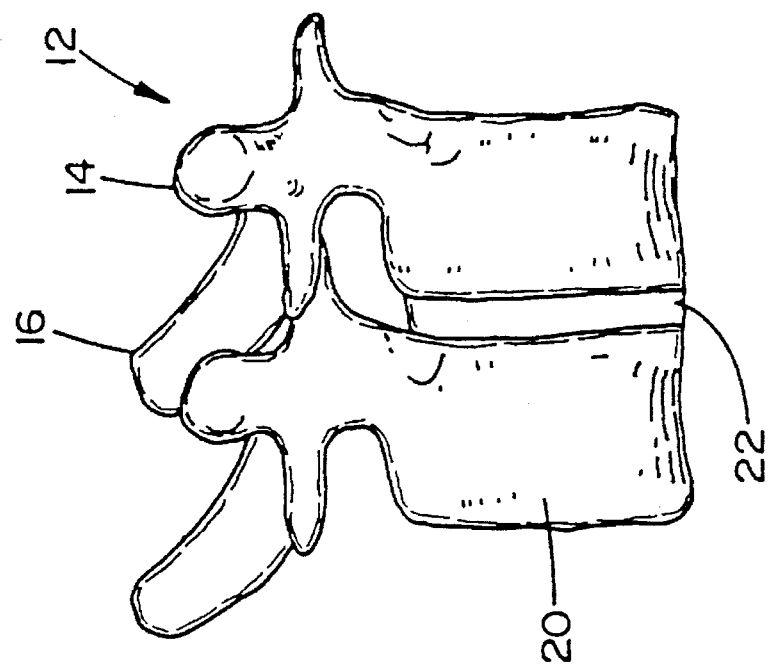
FIG. 2 is a side view of sequentially aligned vertebral bones, such as are found in the cervical, thoracic, or lumbar spine.
Figure 1:
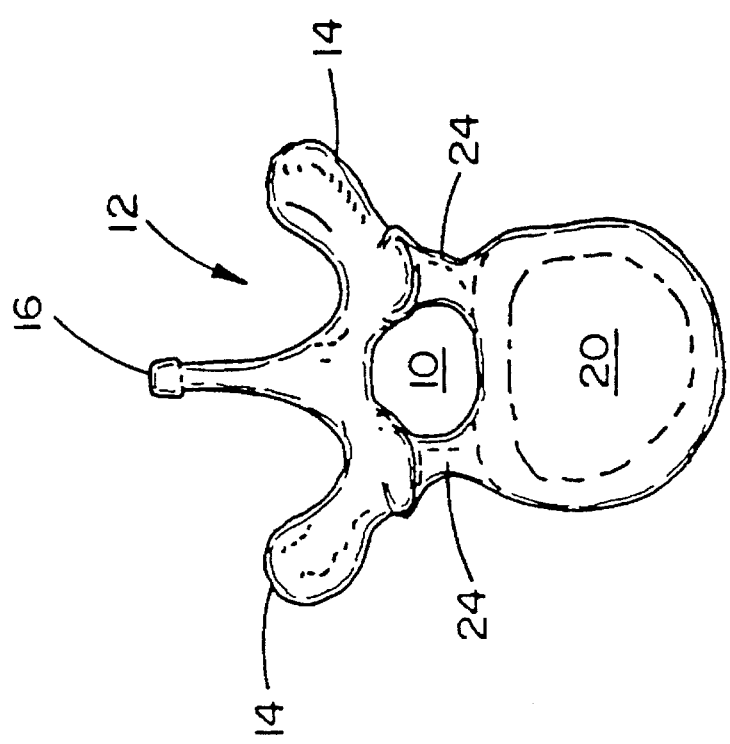
FIG. 1 is a top view of a vertebral bone characteristic of those of the cervical, thoracic, and lumbar spine.
Figure 4:
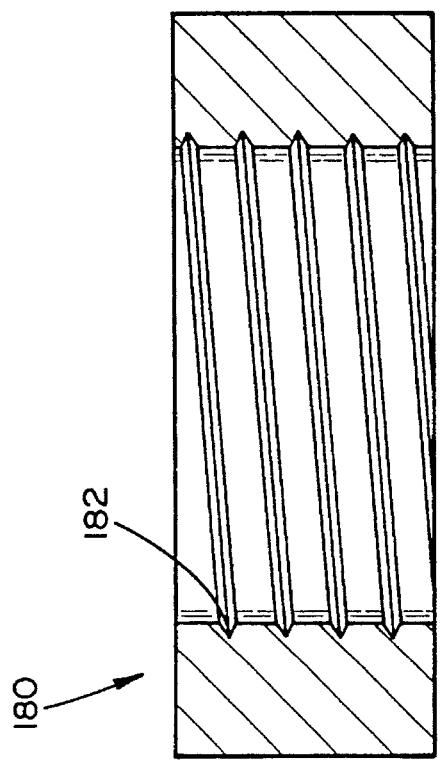
FIG. 4 is a side cross-section view of the tightening nut of the present invention.

Referring now to FIG. 4, a tightening nut 180 comprising an interior threading 182 which is designed to engage the outer upper surface 113 of the recess 110 and be rotationally translated downward on the threadings 115 thereof is shown. This downward translation causes the nut 180 to apply the inwardly directed radial force necessary for the slots 114 to be closed, thereby narrowing the opening 112 and crush locking the inner surface 111 of the opening against a shaft portion which may be disposed in the recess 110. The shaft is thereby locked in position relative to the blade 100. The Referring now to FIG. 6, a first embodiment of the body portion 200 of the present invention is shown in a side view. The body 100 comprises a generally cylindrical shape which may be conceptually separated into a shaft portion 202, and an upper rod receiving portion 206, each of which shall be described more fully hereinbelow.

First, with respect to the shaft portion 202, the body portion 200 is designed to be slideably mounted in the cylindrical recess 110 of the blade portion 100 (see FIG. 3) and as such has a generally cylindrical shape. This shaft 202 must be long enough to provide a sufficiently large stroke within the recess 110 so that the height of the intermediate and upper portions 204,206 of the body 200 may be varied enough to compensate for misalignments of the support rod relative to the entire assembly. The shaft 202 is cylindrical in shape for the additional purpose of permitting the body 200 to be rotated within the recess 110, so that the rod receiving means, as described more fully hereinbelow with respect to the upper portion, may be positioned to receive the rod independent of normal deviations from the standard axial disposition of the rod.

The upper portion 204 of the generally cylindrical body 200 includes a pair of upwardly extending members 204a, 204b which define therebetween a vertical channel 222 in the top of the body. The upwardly extending members further include a exterior threading for receiving thereon a top locking nut (see FIG. 5). The rod receiving channel 222 comprises a curvate bottom 224; the depth thereof being established such that a circular support rod which is positioned in the rod receiving channel 222 may nests below the tops of the upwardly extending members 204a,204b, which would prevent the top locking nut (such as shall be described with reference to FIG. 5) from engaging the exterior threading on the upwardly extending members.

Figure 5:
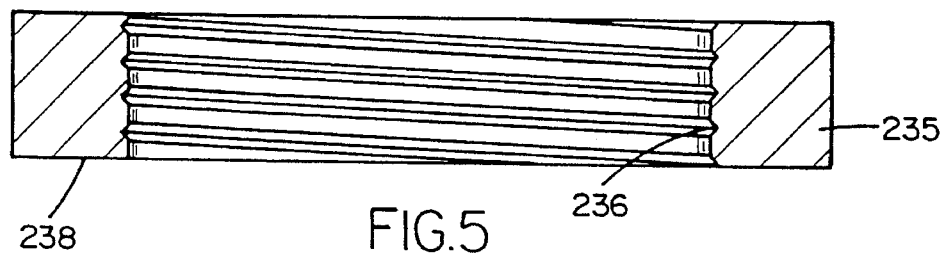
FIG. 5 is a side view of the first embodiment of the shaft portion of the present invention.

Referring now to FIG. 5, a top locking nut 235 is shown, in side cross-section views. The top locking nut 235 comprises an inner threading 236 which is intended to mate with the threading 226 on the upper portion 206. The bottom surface 238 of the nut 235 is intended to seat against the top surface 242 of the support rod (or against an optional rod securing sleeve 240 as described with respect to FIG. 8), but is permitted to rotate relative to the rod, therein providing a means for driving the rod downward (as described more fully with respect to the assembly of the device as shown in FIG. 7).

Figure 6:
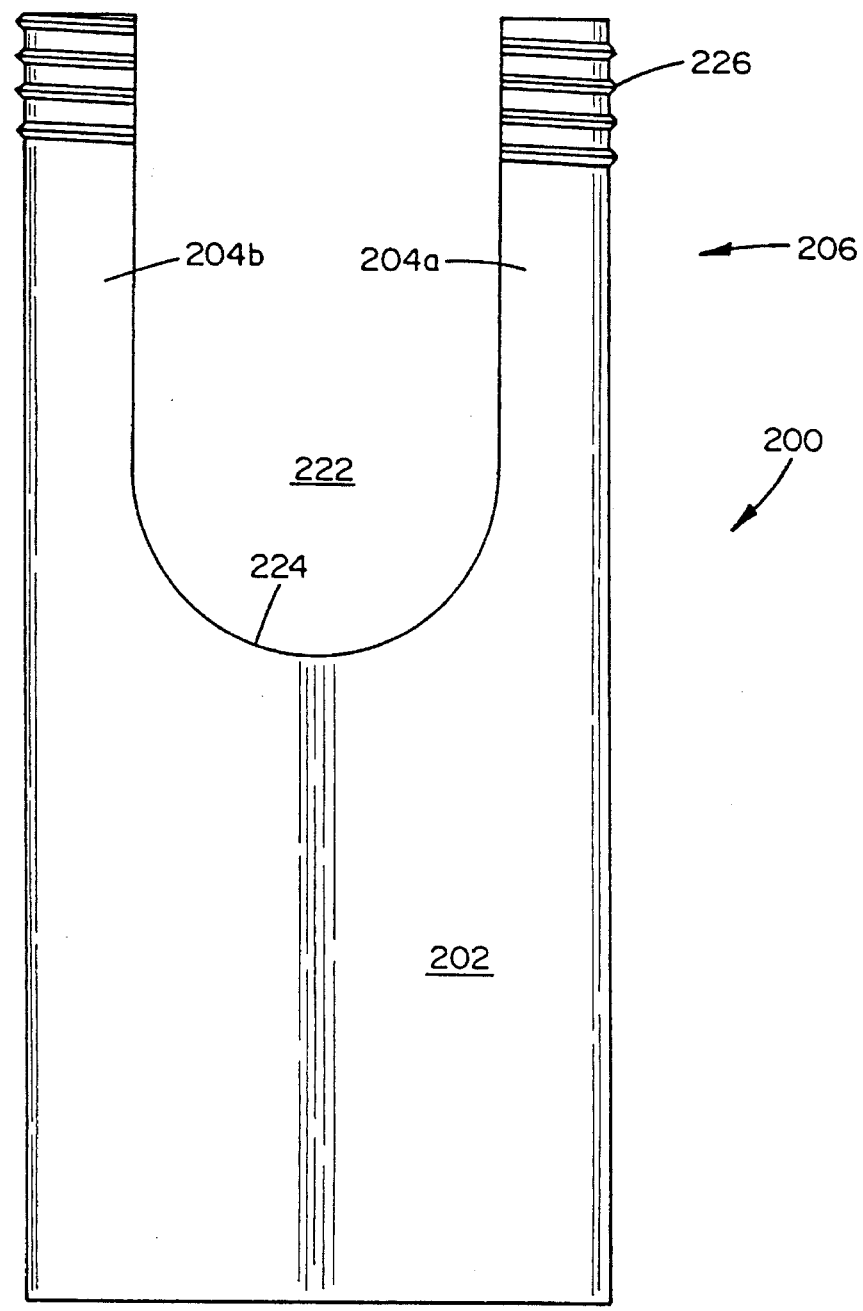
FIG. 6 is a side cross-section view of the top locking nut of the present invention.
Figure 7:
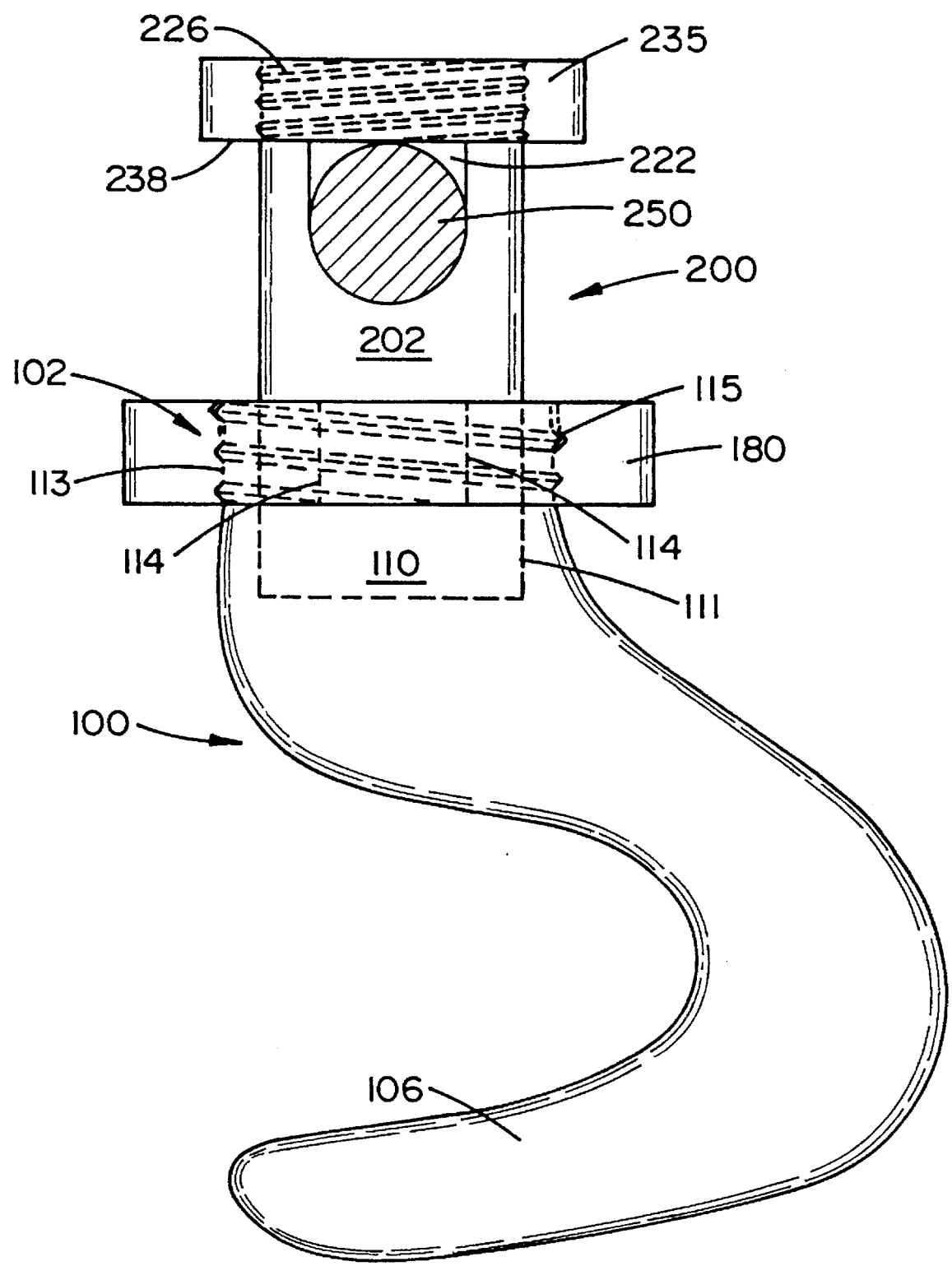
FIG. 7 is a side view of a fully assembled hook which is a first embodiment of the present invention shown with a support rod secured therein.

With reference now to FIG. 7, which illustrates the fully assembled hook device of the first embodiment, including the support rod 250, a step by step method of implantation is described, wherein each element set forth with respect to FIGS. 3–6 is utilized. (It shall, however, be understood that in a true surgical procedure, the blade portion 100 would be rotated 90 degrees relative to the axis of the rod—as opposed to the transverse orientation shown in FIG. 8—so that the rod 250 and the flat extending member 106 of the blade portion 100 are substantially parallel.)

First the blade portion 100 is mounted to the lamina, such that the flat extending member 106 thereof is disposed beneath the lamina and the body receiving portion 102 is disposed above the lamina. The shaft portion 202 of the body 200 is then positioned in the cylindrical recess 110 at the proper height and rotational orientation. (As introduced above, it may be desirable for the shaft to be coupled within the recess 110 so that it may not be fully removed therefrom, but may be raised and rotated as necessary.)

Once properly set the tightening nut 180 is introduced onto the threading 115 of the blade portion 100. It is understood that the tightening nut 180 may have been placed on the outer tapered surface 113 prior to the introduction of the shaft 202 in the recess 110, or the tightening nut may be dropped over the body 200 to engage the threading 115. Tightening of the nut 180 on the outer threading causes the nut 180 to translate downward on the outer tapered surface 113, thereby applying an inward force against it, and closing the slots 114. The inner surface 111 of the recess 110 is then locked to the shaft 202 preventing further movement thereof relative to the blade portion 100.

Once the shaft portion 202 is locked in position, the support rod 250 may be positioned in the rod receiving channel 222. The top locking nut 235 is then threadably mated to the threading 226 of the upper portion 206, the downward translation of which causes the the bottom surface 238 of the nut 235 to seat against the top of the rod 250. The nut 235, thereby, supplies the necessary force to hold the rod securely in the channel 222.

Figure 8:
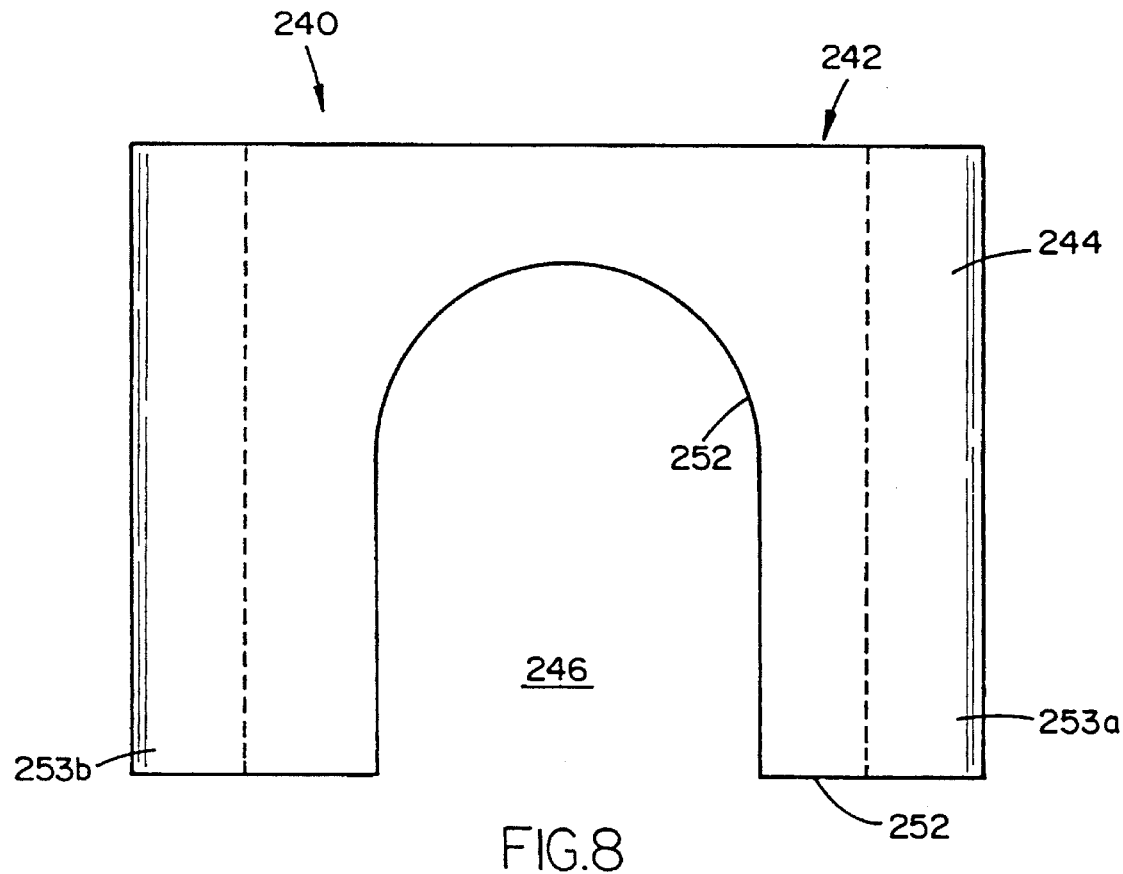
FIG. 8 is a side view of the rod securing sleeve which may be utilized with variations of this invention.

Referring now to FIG. 8, an optional rod securing sleeve 240, which may be introduced over the support rod 250 prior to the engagement of the top locking nut 235 is shown. The rod securing sleeve comprises a hollow cylindrical body 244 having a flat annular top surface 242 and a curved bottom surface 252. In fact, the bottom surface 252 is so curved as to have an upside-down U-shape defined by a pair of downwardly extending members 253a,253b formed of the cylindrical body 244. These downwardly extending members 253a,253b, in turn, define diametrically opposing vertical slots 246, which together provide a passage through the bottom of the sleeve for cupping a rod placed therethrough. The interior diameter of the sleeve 240 is equal to the outer diameter of the body 200, so that it may be placed over the upper portion 206 thereof.

Figure 9:
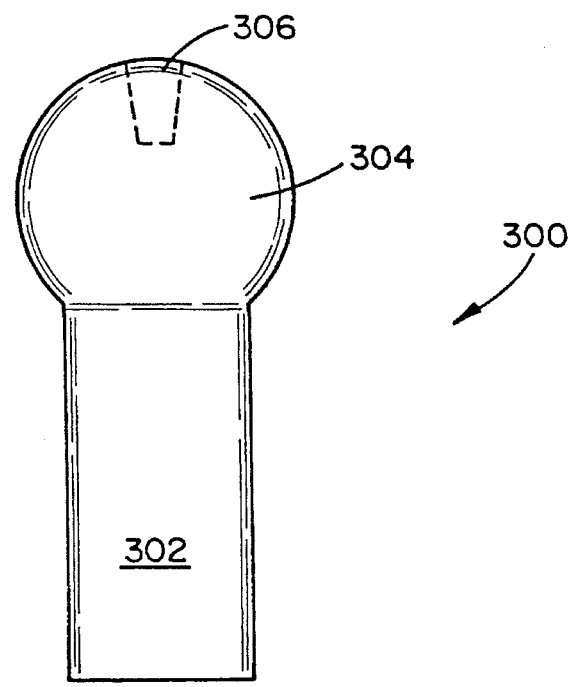
FIG. 9 is a side view of a shaft portion having a semispherical head, which is an aspect of a second embodiment of the present invention.

Referring now to FIG. 9, the body portion 300 of the second variation of the present invention, wherein the rod receiving portion of the hook device may be polyaxially angulated relative to the blade portion 100 (and the body portion 300), is shown. The body comprises a shaft portion 302, which is similar in all respects to the shaft portion 202 of the body 200 of the first embodiment. In addition, however, the body 300 has only a semi-spherical head 304 at the distal end of the shaft 302. This semi-spherical head 304 further comprises a recess 306 in the top thereof for coupling to a post (not shown) so that the surgeon using the device may raise and lower the body portion 300 relative to the blade portion 100 more easily. It is preferable that this recess 306 be threaded so that the post may engage the head 304 via a threaded end.

Figure 10:
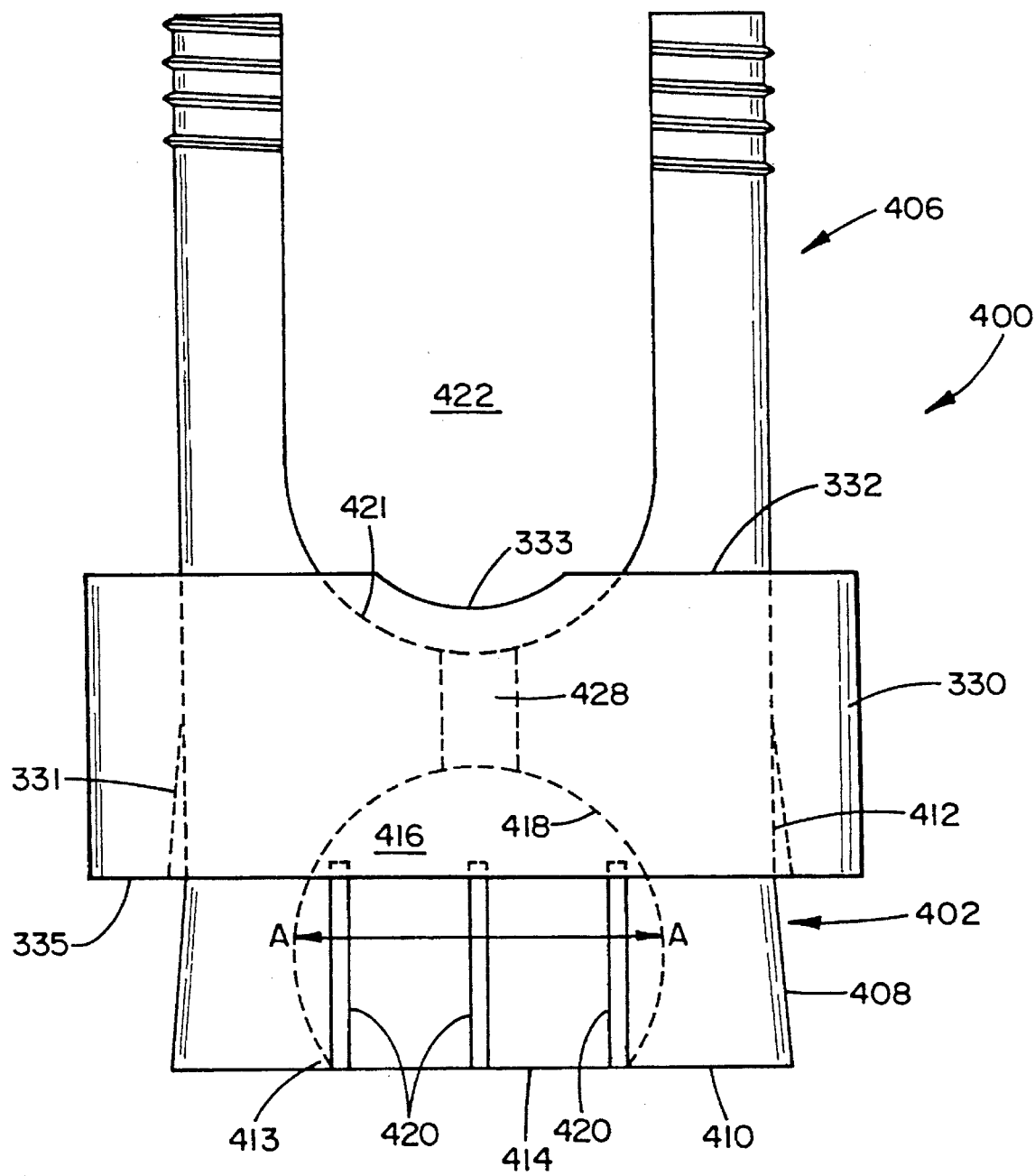
FIG. 10 is a side view of a polyaxial coupling element of the second embodiment of the present invention.

Referring now to FIG. 10, the polyaxial rod coupling element 400 of the second embodiment is shown in a side view, wherein a locking ring 330 is disposed thereabout the element. The coupling element comprises a lower and an upper portion 402,406, respectively. First with respect to the lower portion, the exterior surface 408 of the coupling element is tapered in the elongate direction such that the body is wider at the bottom 410 than at the top 412 of the lower portion 402. The bottom 410 of the element includes an expandable and contractable opening 414, defined by annular lip 413, which forms the mouth of an expandable and contractable interior chamber 416. The diameter of the opening 414, when otherwise unaffected by external deflecting forces, is more narrow than the maximum diameter A—A of the interior chamber 416. The interior chamber 416 has a generally curvate inner surface 418 which is correspondingly shaped to receive the semi-spherical head 304 of the body 300.

The exterior surface of the lower portion 402 further includes a series of slots 420 which extend vertically upward from the bottom 4210 of the element to a point which is closer to the top 412 of the lower portion 402 than the maximum horizontal diameter A—A of the interior chamber. The slots 420 are provided in order that the application of an external deflecting force may widen or narrow the opening 414 therein permitting the insertion of an object, such as the head 304, which is larger than the undeflected diameter of the opening 414, or conversely, providing for the retention of an object such as the same.

The upper portion,406 of the coupling element 400 is substantially similar to that of the body 200 of the first embodiment, but for an axial passageway 428 extending from the bottom of the channel 422 to the interior chamber 416, so that the surgeon may access the recess 306 in the head 304 of the body portion 300. The coupling element 400 further includes a locking ring 330 which comprises a contiguous annular element having an inner diameter which is equal to the outer diameter of the lower portion 402 at the top 412 thereof. The inner surface 331 of the locking ring may be tapered slightly at the bottom theeof to match the upper portion of the taper of the lower portion 402. In its initial disposition, about the coupling element 400, the ring 330 is positioned so that the upper annular surface 332 thereof is above the curved bottom 321 of the channel 422. In this disposition, the bottom 335 of the ring 330 extends to a point below the uppermost part 412 of the lower portion 402, the point being determined by the diameters of the tapered lower portion 402 and the tapered inner surface 331 of the ring 330.

The upper surface 232 of the locking ring 330 comprises a notch 233 which is ideally suited and shaped for supporting thereon the rod 250. The locking ring is, therefore, designed to be positioned at the top 412 of the lower portion of the coupling element 400 and for the rod 250 to seat in the notch 233 thereof. Application of pressure downward by the rod causes the ring 330 to crush the inner surface of the interior volume 416 against the head 304.

It shall be understood that a dowel, protuberance, or other suitable means may be provided at or above the top 412 of the lower portion 402 so that the ring 330 may not be easily moved upward, and thereby preventing separation of the locking ring during handling prior to use. In addition, it shall be further understood that in its properly inserted orientation, it is desirable for coupling element 400 to be rotated approxiamtely 90 degrees relative to the blade portion 100 such that the channel 422 may receive therein a rod which is aligned substantially colinearly with the lower branching portion 106 of the blade portion 100.

Figure 11:
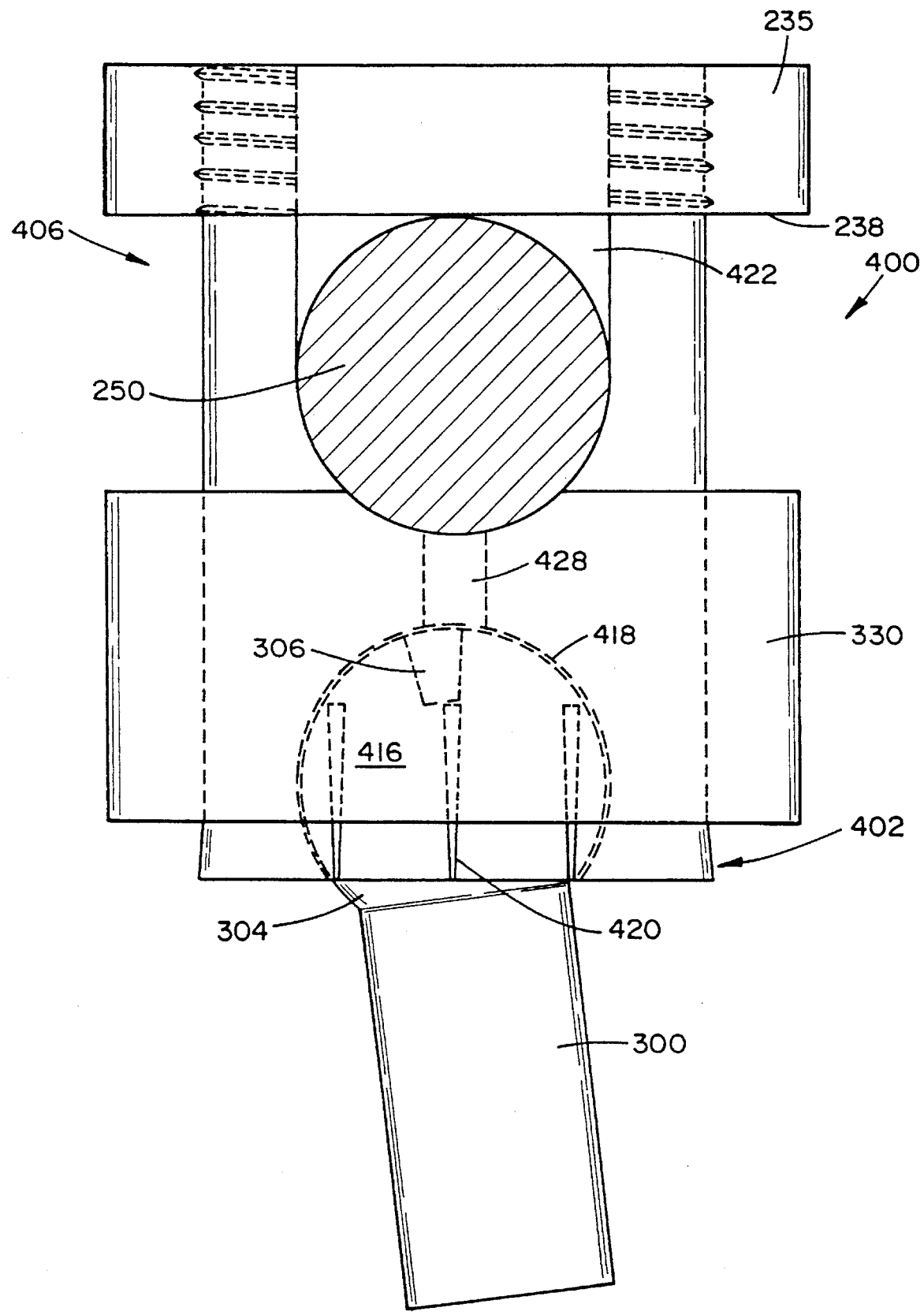
FIG. 11 is a side view of the shaft portion of the second embodiment of the present invention, shown with the semispherical head thereof locked within the interior chamber of the coupling element of FIG. 10, wherein the coupling element has secured and locked a support rod therein.

With reference now to FIG. 11, which shows a side view of the coupling element 400 locked to the semi-spherical head 304 of the body portion 300, the preferred method of implantation and assembly is described hereinbelow. First, the blade portion 100 (see FIGS. 3 and 7) is positioned on the lamina (not shown) such that the flat extending member 106 thereof is positioned under the lamina and in the spinal canal. It is critical that the flat extending member 106 be positioned as close to flush against the underside of the lamina as possible. Then the body portion 300 is locked in place relative to the blade 100, in a manner identical to the way described with respect to the first embodiment; the tightening nut 180 being used to crush lock the cylindrical recess 110 of the blade portion 100 to the shaft portion 302 of the body 300.

Once the body is rigidly positioned relative to the lamina, the head 304 thereof is inserted into the interior chamber 416 of the coupling element 400. (This step may, of course, be taken prior to the locking of the shaft 302 to the blade portion 100, however, in such a case, the surgeon may need to polyaxially orient the coupling element such that a threaded post may be inserted down the axial passageway 428 of the coupling element 400, into the interior chamber 416, and couple with the recess 306 in the semi-spherical head 304, so that the shaft 302 may be raised and lowered relative to the blade portion 100 to attain the proper height ajustment.)

At this point in the assembly process, the locking ring 430 has not yet been forced downward along the outwardly tapered lower portion 402, thereby providing the coupling element 400 with the capacity to rotate and angulate relative to the shaft 302 (and the blade portion 100). This permits the support rod 250 to be properly nested within the rod receiving channel 422 in spite of small misalignments of the rod. At this stage of the assembly, the the support rod 250 is prevented from translating downward fully onto the bottom surface of the channel 422 by the locking ring 330.

Once the proper angulation of the coupling element to the body 300, and the secure nesting of the rod 250 within the receiving channel 422, have been established, the top locking nut 235 (as shown in FIG. 6) is threaded onto the upper portion 406 of the coupling element 400. The lower surface 238 of the nut 235 seats against the top of the rod 250. As the nut 235 rotates, and descends relative to the coupling element 400, the rod 250 is driven downward. This motion forces the locking ring 330 to translate downward along the lower portion 402 of the coupling element 400. By descending along the tapered lower portion 402 of the element, the locking ring 330 provides an inwardly directed deflecting force which causes the slots 420 in the lower portion 402 of the element to narrow so that the ring may proceed downward. This deflection inward causes the inner surface 418 of the interior chamber 416 to crush lock against the head 304 of the body 300. This clamping force locks the angulation of the coupling element 400 relative to the body 300. Ultimately, once the locking ring 330 cannot be translated down any further, the downward force of the nut 235 against the rod 250 causes it to be locked between the nut 235 and the top surface of the locking ring 330. This locking prevents the rod 250 from sliding relative to the assembled structure. The full insertion of the top locking nut 235, therefore, locks the rod 250 to the coupling element 400, as well as the body 300 to the coupling element 400.

As was described above with respect to FIG. 8 and the first embodiment, it is understood that a rod retaining sleeve 240 may be introduced between the top locking nut 235 and the rod 250. The rod securing sleeve 240 may be utilized if additional securing surface is necessary to hold the rod 250 rigidly in the channel 422.

While there has been described and illustrated embodiments of lamina hook device having variable length body portions, one of which further includes a polyaxial coupling element, it will be apparent to those skilled in the art that variations and modifications are possible without deviating from the broad spirit and principle of the present invention. The present invention shall, therefore, be limited solely by the scope of the claims appended hereto.

We claim:

1. A polyaxial hook assembly for use with orthopedic rod implantation apparatus, comprising:

a blade portion, having a curved shape for cupping the lamina, a flat extending member for disposition beneath a lamina, and a cylindrical recess in a portion of the blade portion which is disposed above the flat extending member, said cylindrical recess having a selectively contractable upper portion;

a body including
a shaft portion, slideably mountable within said cylindrical recess, whereby selective contraction of said upper portion of said cylindrical recess crush locks said shaft to said blade portion,
a pair of upwardly extending members defining therebetween a channel in the top thereof for receiving therein a support rod of said orthopedic rod implantation apparatus, and
an external surface threading disposed on said pair of upwardly extending members;

means for selectively contracting said selectively contractable upper portion of said cylindrical recess for locking said shaft portion to said blade portion; and a top locking nut which is mateable with said surface threading on said upper portion.

2. The polyaxial hook assembly as set forth in claim 1, wherein said contractable upper portion of said cylindrical recess comprises at least one slot, a taper, and a threading; and wherein said means for selectively contracting said cylindrical recess comprises a tightening nut, the selective engagement of which contracts the at least one slot, thereby contracting the recess and locking the shaft portion in the cylindrical recess.

3. The polyaxial hook assembly as set forth in claim 1, further comprising a rod securing sleeve having a hollow cylindrical body including opposing vertical slots, said sleeve being positionable around said body for securing said rod within said rod receiving channel with said rod extending through said vertical slots.

4. A polyaxial hook assembly for use with orthopedic rod implantation apparatus, comprising:

a blade portion, having a curved shape for cupping the lamina, a flat extending member for disposition beneath a lamina, and a cylindrical recess in a portion of the blade portion which is disposed above the flat extending member, said cylindrical recess having a selectively contractable upper portion;

a body including, a shaft portion, slideably mountable within said cylindrical recess, whereby selective contraction of said upper portion of said cylindrical recess crush locks said shaft to said blade portion, and a semi-spherical head;

means for selectively contracting said selectively contractable upper portion of said cylindrical recess for locking said shaft portion to said blade portion;

a coupling element, polyaxially mounted to said semi-spherical head, said coupling element comprising
an expandable and contractable interior chamber for receiving therein said semi-spherical head, said interior chamber further having an expandable and contractable opening for receiving therethrough said semi-spherical head,
a pair of upwardly extending members defining therebetween a rod receiving channel formed in a top thereof for receiving therein a support rod of said orthopedic rod implantation apparatus, and
a surface threading disposed on an exterior portion of said pair of upwardly extending members;

a locking ring mounted around said coupling element, the downward translation of said ring providing a force which causes said interior chamber and said opening thereof to contract, therein locking the coupling element to the semi-spherical head; and a top locking nut, mateable with said surface threading.

5. The polyaxial hook assembly as set forth in claim 4, wherein said contractable upper portion of said cylindrical recess comprises at least one slot, a taper, and a threading; and wherein said means for selective contraction of said cylindrical recess comprises a tightening nut, the selective engagement of which contracts the at least one slot, thereby contracting the recess and locking the shaft portion in the cylindrical recess.

6. The polyaxial hook assembly as set forth in claim 5, wherein said coupling element further comprises at least one vertical slot extending upward from said opening, therein rendering said interior chamber and said opening expandable and contractable.

7. The polyaxial hook assembly as set forth in claim 6, wherein a portion of said coupling element which contains said interior chamber comprises an exterior surface taper, said portion being wider at said opening, whereby the downward translation of said locking ring causes the interior chamber and said opening to contract.

8. The polyaxial hook assembly as set forth in claim 7, wherein a bottom surface of said top locking nut seats against a top surface of a rod securing sleeve, and the support rod seats against a top surface of said locking ring, the downward translation of said top locking nut thereby causing said support rod to be crush locked between said rod securing sleeve and said locking ring.

9. The polyaxial hook assembly as set forth in claim 8, wherein said downward translation of said nut on said threading of said upwardly extending members causes the downward translation of said locking ring to crush lock the semi-spherical head within said interior chamber.

10. The polyaxial hook assembly as set forth in claim 5, further comprising a rod securing sleeve, positionable around, and in rod securing relationship with, said rod receiving channel for securing said support rod therein.

11. An orthopedic rod implantation apparatus, comprising:
   at least one elongate rod;
   a plurality of polyaxial hook assemblies for coupling said elongate rod to lamina of a spine, each of said hook assemblies including:
   a blade portion, having a curved shape for cupping the lamina, a flat extending member for disposition beneath a lamina, and a cylindrical recess in a portion of the blade portion which is disposed above the flat extending member, said cylindrical recess having a selectively contractable upper portion;
   a body including, a shaft portion, slideably mountable within said cylindrical recess, whereby selective contraction of said upper portion of said cylindrical recess crush locks said shaft to said blade portion, and a semi-spherical head;
   means for selectively contracting said selectively contractable upper portion of said cylindrical recess for locking said shaft portion to said blade portion;
   a polyaxial coupling element, mounted on said semi-spherical head having a pair of upwardly extending members defining therebetween a channel for receiving and securing therein the support rod.

12. The rod implant apparatus of claim 11, wherein said contractable upper portion of said cylindrical recess comprises at least one slot, a taper, and a threading; and wherein said means for selectively contracting said cylindrical recess comprises a tightening nut, the selective engagement of which contracts the at least one slot, thereby contracting the recess and locking the shaft portion in the cylindrical recess.

13. The rod implant apparatus as set forth in claim 11, wherein said pair of upwardly extending members further include an exterior threading, and further comprising a top locking nut which is mateable with said exterior threading.

14. The rod implantation apparatus as set forth in claim 11, wherein said polyaxial coupling element includes lower and upper portions, said lower portion including a taper wherein the bottom of the portion is wider than the top, said coupling element including:
   at least one vertical slot formed in said lower portion extending upward from a bottom of said lower portion,
   an opening in said bottom of said lower portion, for receiving therethrough said semi-spherical head, said opening being expandable and contractable by via forces applied to said at least one vertical slot;
   an interior chamber disposed within said lower portion, for receiving therein said semi-spherical head; and
   a threading on the exterior of said pair of upwardly extending members.

15. The rod implantation apparatus as set forth in claim 14, further comprising:
   a locking ring mounted around said lower portion, the downward translation of said ring applying an inward force to said at least one vertical slot and therein locking the semi-spherical head within the coupling element; and
   a top locking nut which is mateable with said exterior threading.

16. The polyaxial hook assembly as set forth in claim 15, wherein said coupling element further comprises at least one vertical slot extending upward from said opening, therein rendering said interior chamber and said opening expandable and contractable.

17. The polyaxial hook assembly as set forth in claim 16, wherein a portion of said coupling element which contains said interior chamber comprises an exterior surface taper, said portion being wider at said opening, whereby the downward translation of said locking ring causes the interior chamber and said opening to contract.

18. The polyaxial hook assembly as set forth in claim 17, wherein a bottom surface of said top locking nut seats against a top surface of a rod securing sleeve, and the support rod seats against a top surface of said locking ring, the downward translation of said top locking nut thereby causing said support rod to be crush locked onto said locking ring.

19. The polyaxial hook assembly as set forth in claim 18, wherein said downward translation of said nut on said exterior threading of said upwardly extending members causes the downward translation of said locking ring to crush lock the semi-spherical head within said interior chamber.

20. The polyaxial hook assembly as set forth in claim 11, further comprising a rod securing sleeve comprising a hollow cylindrical body, having opposing vertical slots, said sleeve being positionable around said body for securing said rod within said rod receiving channel, wherein said rod passes through said vertical slots of said sleeve.

* * * * *